United States Patent [19]

Schweizer et al.

[11] Patent Number: 5,332,181
[45] Date of Patent: Jul. 26, 1994

[54] MOTORIZED STAND

[75] Inventors: Jurgen Schweizer, Westerhofen; Hartmut Gartner, Oberkochen; Joachim Luber, Essingen-Forst, all of Fed. Rep. of Germany

[73] Assignee: Carl Zeiss-Stiftung, Heidenheim, Fed. Rep. of Germany

[21] Appl. No.: 6,248

[22] Filed: Jan. 19, 1993

[30] Foreign Application Priority Data

Feb. 1, 1992 [DE] Fed. Rep. of Germany ....... 4202922

[51] Int. Cl.$^5$ ............................................. F16L 3/00
[52] U.S. Cl. ................................ 248/123.1; 248/280.1; 248/281.1; 248/648; 901/8; 901/9
[58] Field of Search ............ 248/122, 123.1, 648, 248/280.1, 281.1; 350/522; 414/729; 901/8, 9

[56] References Cited

U.S. PATENT DOCUMENTS

| | | | |
|---|---|---|---|
| 4,344,595 | 8/1982 | Heller | 248/280.1 X |
| 4,515,333 | 5/1985 | Pugh | 248/122 |
| 4,548,374 | 10/1985 | Thompson | 248/280.1 X |
| 4,660,798 | 4/1987 | Kinoshita | 248/123.1 X |
| 4,684,088 | 8/1987 | Heller | 248/280.1 X |
| 4,741,607 | 5/1988 | Heller | 350/522 |
| 4,835,450 | 5/1989 | Suzuki | 901/9 X |
| 4,867,405 | 9/1989 | Nakamura | 248/123.1 X |
| 4,904,152 | 2/1990 | Doi | 901/9 X |
| 4,943,296 | 7/1990 | Funakubo | 901/8 X |
| 4,970,448 | 11/1990 | Torii | 901/9 X |
| 4,986,724 | 1/1991 | Steinmetz | 414/729 |
| 5,049,028 | 9/1991 | Asano | 901/9 X |
| 5,055,755 | 10/1991 | Ozawa | 901/9 X |

FOREIGN PATENT DOCUMENTS

| | | | |
|---|---|---|---|
| 0386842 | 9/1990 | European Pat. Off. | A61B 6/00 |
| 695881 | 9/1940 | Fed. Rep. of Germany | 248/654 |
| 4032207 | 4/1991 | Fed. Rep. of Germany | A61B 19/00 |

Primary Examiner—J. Franklin Foss

[57] ABSTRACT

A motorized stand for positioning medical therapeutic or diagnostic instruments is mechanically coarsely balanced by weights. A defined positioning of the medical instrument is determined by means of several drive units with integrated angle transducers. Operating safety is additionally ensured, in the event of failure of a drive unit, by the use of two angle transducers per drive unit. One angle transducer is coupled to the drive motor of each drive unit. The other angle transducer is independent of the drive motor.

39 Claims, 2 Drawing Sheets

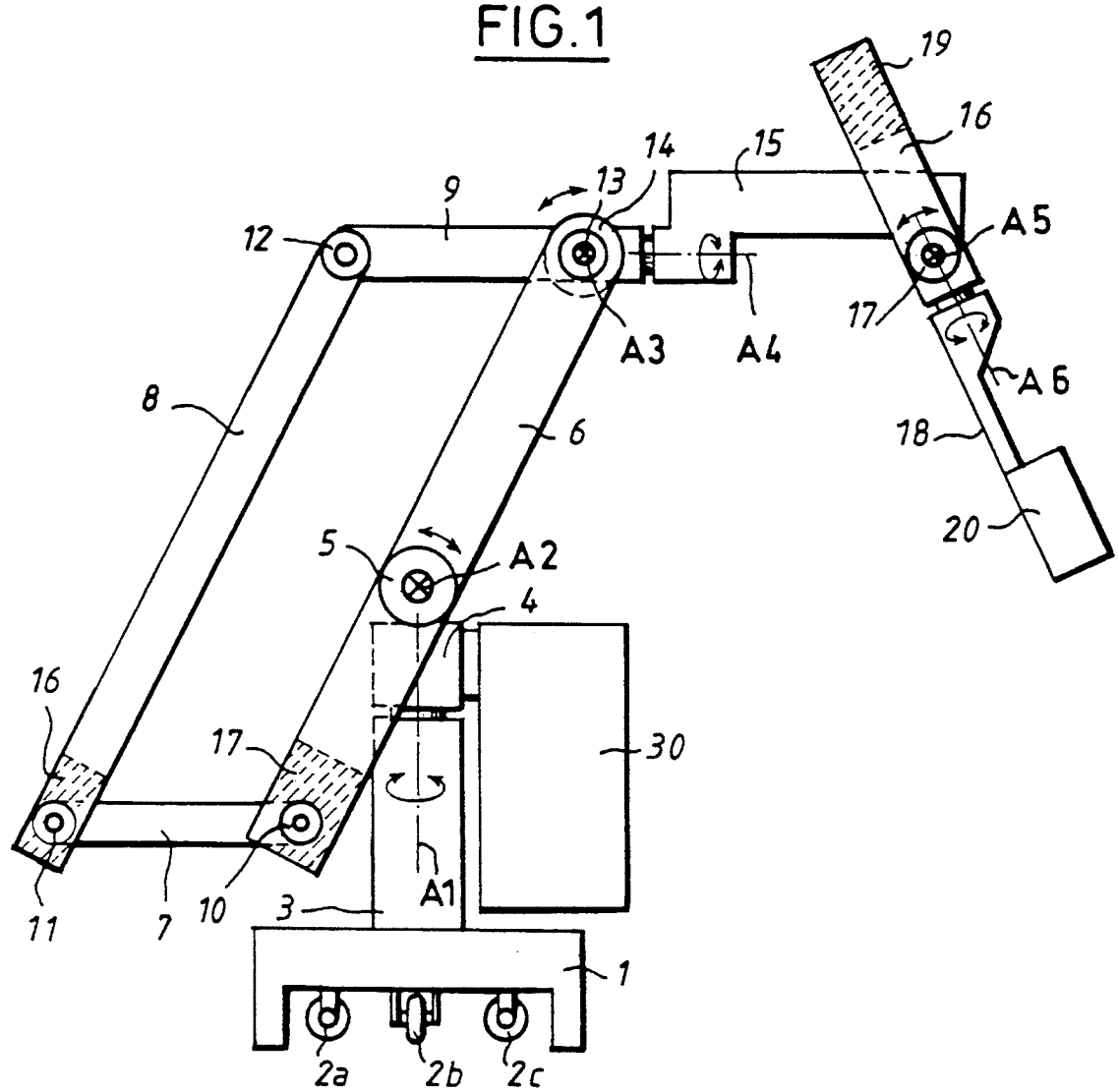
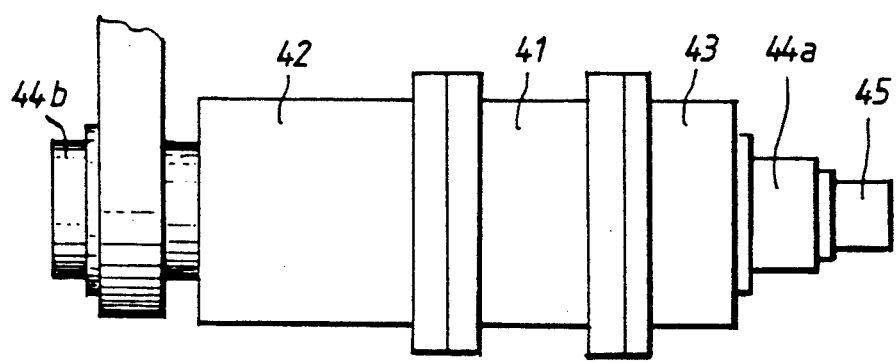

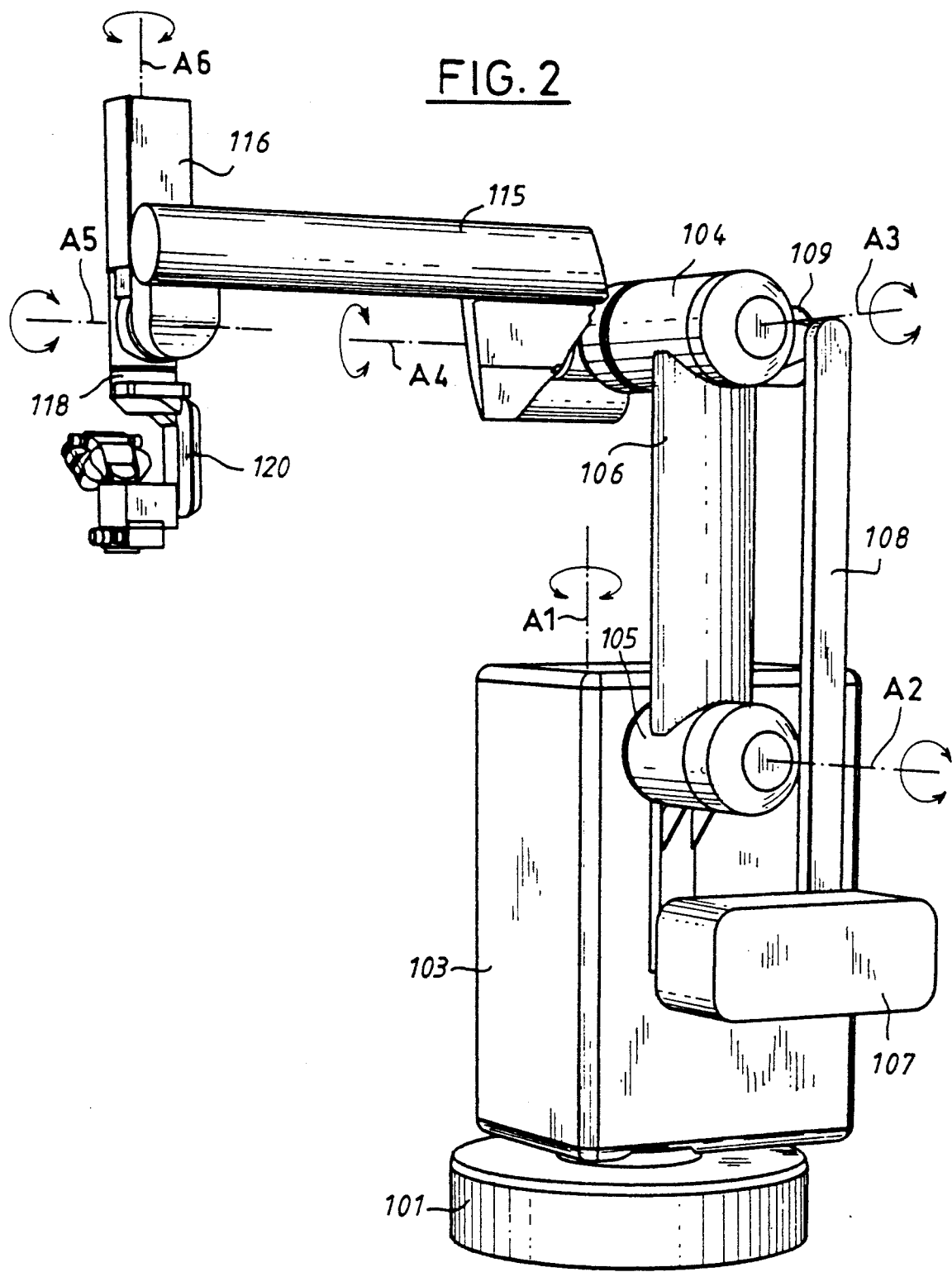

MOTORIZED STAND

This invention relates to a motorized stand for positioning medical diagnostic or therapeutic instruments.

BACKGROUND OF THE INVENTION AND PRIOR ART

Conventional stands in medical use offer the possibility of manually positioning various diagnostic or therapeutic instruments in up to six degrees of freedom. A manual stand of this kind is described, e.g., in European Patent 0,023,003. However, a series of disadvantages for the surgeon results from manual operation. Thus, inadvertent erroneous movements require a subsequent time-consuming and complicated correction. It is furthermore found to be disadvantageous that in each case mechanically balanced systems are exactly balanced only for a defined instrument weight. This means that a change of the instrument weight requires a rebalancing of the stand system with an accuracy of about 100 g. Such a rebalancing during an operation, after a possible instrument change, is extremely troublesome and complicated. Furthermore, even with well balanced mechanical stand systems, the acceleration or braking of the instrument motion requires a certain operating force proportional to the acceleration or braking, which likewise has a troublesome effect during microsurgical work. Finally, no stereotactic work is in general possible with stands which are moved manually, since the momentary working field is not obtained with usual stands.

An operation microscope is known from German Offenlegungsschrift 4,032,207, which is arranged on a motor-driven, multi-jointed mechanism. Thus, a limited stereotactic use of the operation microscope is possible by means of suitable path and angle detectors. It is considered disadvantageous in this system, however, that no safety measures are provided against a possible failure of the operating electric supply or of the path and angle detectors coupled to it. Thus the multi-jointed mechanism shown has no mechanical balancing that could stabilize the system on failure of the drive units so that at least a limited further procedure could be possible. In addition, with a possible breakdown of the drives, a failure of the path or angle detectors coupled to the drives also results, i.e., a complete system failure potentially results during an operation.

SUMMARY OF THE INVENTION

The object of the present invention is therefore to provide a motorized stand for medical use that makes possible the stereotactic use of the most varied diagnostic or therapeutic instruments. The highest possible safety and positioning accuracy is thus to be ensured, both during normal operation and also during a possible failure of the drive units. In particular, the manual operation of such a stand should still be possible.

This object is achieved by a motorized stand comprising a multi-jointed mechanism having integrated angle transducers and drive units for individual joints of the multi-jointed mechanism, a control unit and means for mechanically balancing the multi-jointed mechanism at least coarsely.

A suitable drive unit includes at least one drive motor with gears, at least one brake, at least one speed transducer and at least two angle transducers to monitor present angle measurement values. The drive unit may include, for example, at least one angle transducer that delivers absolute angle values.

A mechanically coarsely balanced stand, consisting of several stand members, supporting arms or supporting columns, is provided with special drive units which permit a defined positioning of the most varied medical diagnostic or therapeutic instruments. A control unit for this purpose continuously monitors the present angular measurement values of the angle transducers arranged in the individual drive units and hence determines the present space coordinates of the instrument used at any given time. A defined positioning of the instrument is possible by means of corresponding control signals of the control unit to the individual drive units: the control unit provides to each drive unit given reference values that are to be approached, and are then approached by each drive unit in separate control circuits. In this way a stereotactic use of the most varied medical diagnostic or therapeutic instruments can be effected. The control unit furthermore has an input interface which makes possible the input of given target coordinates for the instrument being used, which are then approached by the motorized stand according to the invention, or respectively the instrument being used is positioned in the desired spatial position by means of a motorized stand according to the invention. An input interface of this kind can be used in the most varied embodiments in combination with the motorized stand. Possible are, e.g., various contact-sensitive sensors which are made use of by the surgeon, or optical systems or an input keyboard which respectively serve for the provision of given target coordinates for the motorized stand.

The mechanical balancing of the entire system takes place, in a preferred embodiment, by means of a parallelogram linkage with balancing weights and also a constructional embodiment of given support arms or the corresponding arrangement of balancing weights. Alternatively, such a balancing could also be obtained by the use of springs. It is thus ensured that if a failure of the drive units occurs during an operation, the stand still remains usable at least to a limited degree, and can be moved manually. It is sufficient to balance the entire system mechanically with an accuracy in the kilogram range. However, if necessary it is possible to balance it more accurately. Further important advantages of the motorized stand according to the invention arise, as regards operating safety, from the design of the individual drive units according to the invention, in particular the dimensioning of the gear friction and also the use of two angle transducers per drive unit. Thus the gear friction of the individual drive units is coordinated such that a latitude exists for the weight of the instrument used at any given time, and that mechanical balancing is still provided even when there is a variation of the instrument weight. Thus, when there is a change of equipment during an operation to another medical therapeutic or diagnostic instrument, no additional further mechanical balancing is necessary, which would be complicated or time-consuming. Consequently the most varied medical therapeutic or diagnostic instruments can be used in connection with the motorized stand according to the invention, within a defined weight range. Further advantages relevant to safety result from the use of two angle transducers per drive unit, one of them being coupled to the respective drive motor, while the second operates independently of this drive motor and directly registers the joint motion at any given time. In addition to the continuous mutual measurement value monitoring by the control unit during the usual motorize operation and the resulting high accuracy of positioning, on failure of the drive motor a monitoring of the measurement value of the actual position of movement of the joint is possible by means of the second, independent angle transducer. A knowledge of the present instrument position is thus ensured even in this case. Moreover, by the use of a special absolute angle transducer, the present angle measurement values are always known, even without possible reference measurements.

The abovementioned dimensioning of the gear friction furthermore offers the advantage that even in the case of possible out-of-plumb placement of the motorized stand a system which shows a behavior as still balanced is available and does not move in an uncontrolled manner on its own.

The foot portion furthermore has rollers which can be extended and retracted and which make possible easy operation of the motorized stand as a whole. In a preferred embodiment, these rollers can be extended and retracted by a motor drive.

A motorized stand of such a kind is especially suitable for use in connection with an operation microscope in stereotactic microsurgery. However, the stereotactic use of various other surgical instruments is also possible in combination with the motorized stand. Endoscopes, intra-operative probes, biopsy cannulas, surgical borers or the like instruments are possibilities, for example.

DESCRIPTION OF THE DRAWINGS

Further particulars and also advantages of the motorized stand according to the invention will become apparent from the description of a preferred embodiment with reference to the accompanying drawings, in which FIG. 1 shows a schematic representation of a construction of the motorized stand according to the invention;

FIG. 2 shows an embodiment of the motorized stand according to the invention; and FIG. 3 shows the construction of a drive unit of the motorized stand according to the invention.

DETAILED DESCRIPTION OF PREFERRED EMBODIMENTS

A construction of the motorized stand according to the invention is shown schematically in FIG. 1, the balancing being effected with balancing weights. The motorized stand is arranged on a foot portion (1) which has on its underside rollers (2a, 2b, 2c), which can be extended and retracted by a motor drive, so that easy operation of the motorized drive as a whole is possible. During actual use in an operation, these rollers (2a, 2b, 2c) are retracted in order to ensure that the whole system stand securely. A vertical support column (3) is arranged on the foot portion (1), and on it, in turn, a first stand member (4) is mounted by a first rotary joint for rotation about a vertical axis A1. The stand member (4) or the further components of the motorized stand arranged on it can be rotated in a defined manner about the vertical axis A1 by means of a first drive unit. The first drive unit is integrated into the vertical support column (3) in the illustrated embodiment, and is not visible in this illustration. A parallelogram linkage is fitted to the stand member (4) by means of a second drive unit (5) and a second rotary joint. The parallelogram linkage can be positioned about a horizontal axis A2 relative to the vertical support column (3) or to the first stand member (4) by means of this second drive unit. The parallelogram linkage, consisting of four parallelogram linkage elements (6, 7, 8, 9) and also corresponding rotary joints (10, 11, 12, 13), which rotatably connect these parallelogram linkage elements (6, 7, 8, 9), is displaceable by a third drive unit (14) about the axis A3 or axes parallel to it through the other rotary joints of the parallelogram linkage. The third drive unit (14) is arranged on the rotary joint (13) of the parallelogram linkage. Alternatively, it is possible to arrange the third drive unit on the other rotary joints (10, 11, 12) for the displacement of the parallelogram linkage. The parallelogram linkage has balancing weights (16, 17), which can be arranged, e.g., on the two lower rotary joints (10, 11). The parallelogram linkage thus ensures balancing about the horizontal axes A2 and A3. The first support arm (15) is likewise connected via a rotary joint to the upper parallelogram linkage element (9). The fourth drive unit is integrated into the upper parallelogram linkage element (9) in the illustrated embodiment, and consequently is not visible in this illustration. The first support arm (15) is preferably embodied in a double-cranked construction, so that as large as possible a latitude of movement results for a user who stands beneath the support arm (15). The balancing for rotation about the longitudinal axis A4 is likewise ensured by the special constructional form of this first support arm, as can be clearly seen in FIG. 2. A second support arm (16) is arranged at the outer end of the first support arm (15), and can be moved by a fifth drive unit about the axis A5. The second support arm (16) is connected via a rotary joint to the first support arm (15). The second support arm (16) has a balancing weight (19) at one end, and a third support arm (18) is arranged at the other end, so that balancing is effected about the axis A5 for the rotation about the axis A5. The third support arm (18) is rotatable about its longitudinal axis A6 by a motor drive, which can be effected by a sixth drive unit, which is not shown and likewise is further connected to the second support arm (16) via a rotary joint. It is possible, for example, to arrange the sixth drive unit in the housing of the third support arm (18). The third support arm (18) has at its free end an interface for the most varied medical therapeutic or diagnostic instruments (20). In this embodiment, the instrument used is shown only schematically.

The axes A4, A5, A6 are oriented in space, in the illustrated embodiment, such that they intersect at a point and the so-called robot condition is thereby fulfilled.

The whole structure of the motorized stand according to the invention is designed such that even on failure of the drive units, a mechanically balanced system is still available. This is achieved by balancing by means of the parallelogram linkage and the suitable supplementary weights (10, 11) and also the supplementary weight (19) on the second support arm (16) and the corresponding constructional formation of the first support arm (15). It is additionally ensured, by the coordination of the gear frictions in the six drive units used, that the weight of the respective instrument can fluctuate in a given weight range without adversely affecting the motorized or manual use. The gear frictions must be set up such that a manual operation of the motorized stand is still possible. Accordingly, for example, a quick instrument change during an operation is possible without having to carry out time-consuming balancing procedures.

Furthermore, a control unit (30) which controls the individual drive units in a defined manner is provided for the operation of the motorized stand. This control unit (30) is preferably arranged in a suitable cabinet above the foot portion (1) of the motorized stand. In order to ensure a defined positioning of the motorized stand, the control unit (30) must continuously monitor the present space coordinates of the respective instrument. This takes place by continuous reading out from the angle transducers, which are coupled to each drive unit. With known geometrical measurements of the motorized drive or of the individual elements and stand members, the determination of the instrument position in the stand coordinate system is accordingly possible at any time. If in addition the relationship between the stand coordinate system and the patient coordinate system is known, the stereotactic use of the motorized stand and of the instrument arranged on it is ensured.

The provision of given target coordinates for the respective therapeutic or diagnostic instrument by the surgeon takes place through an input interface, which is coupled to the control unit. As possible input interfaces, contact-sensitive sensors, optical systems, joysticks, or input keyboards are possibilities. The control unit then provides for each drive unit given reference values, which are approached. These reference values are then approached in a defined manner via separate control circuits for the respective drive units.

An embodiment of the motorized stand according to the invention is illustrated in perspective in FIG. 2. A cabinet (103), in which the control unit is accommodated, is arranged above the round foot portion (101). The vertical support column visible in FIG. 1 and the first stand member are consequently not visible in this illustration. The cabinet (103) is connected to the first stand member and is rotated with this stand member about the first vertical axis A1. A parallelogram linkage is arranged on the first stand member (not shown) via a second drive unit (105) and a rotary joint. The parallelogram linkage, consisting of four parallelogram linkage elements (106, 107, 108, 109) is moveable, about a horizontal axis A2 by means of the second drive unit (105) and the rotary joint, relative to the cabinet (103) or to the foot portion (101) and the first stand member and the vertical support column. The four parallelogram linkage elements (106, 107, 108, 109) are movable relative to each other by means of rotary joints, not visible in this illustration, in the corners of the parallelogram linkage. The lower parallelogram linkage element (107) is provided with a balancing weight for balancing. The rotary joint between the parallelogram linkage elements (106) and (109) is provided with a third drive unit (104), by means of which a motor-driven relative displacement of the parallelogram linkage is possible per se. The rotary motion here takes place about a further horizontal axis A3 which passes through the rotary joint. Another arrangement of the third drive unit in one of the other corners of the parallelogram linkage is also possible. A first support arm (115), as an extension of the uppermost parallelogram linkage element (109), is arranged via a rotary joint, which can be rotated about its longitudinal axis A4 by means of a fourth drive unit. Balancing for rotation about the longitudinal axis A4 is achieved by the special constructional form of the first support arm (115), as is clear in this perspective illustration. The fourth drive unit necessary for this is not visible in this illustration and can be accommodated, for example, in the upper parallelogram linkage element (109). The double-cranked construction of the first support arm (115) can be clearly discerned in this illustration, and has the consequence of an optimum freedom of movement for the surgeon operating beneath it. A second support arm (116), including a fifth drive unit (not shown), is mounted at the outer end of the first support arm (115). The second support arm (116) can be rotated about a further axis A5 by means of the rotary joint and the fifth drive unit. One end of the support arm (116) is provided with balancing weights, while a third support arm (118) is arranged at the opposite end. This support arm (118), in turn, is movable by a motor drive about its long axis A6, by a corresponding rotary joint and a sixth drive unit (likewise not shown). An interface is situated at the end of this support arm (118), to which, in this embodiment, an operation microscope (120) is attached as the medical therapeutic or diagnostic instrument.

The construction of the respective drive units will be described below with reference to FIG. 3. The design of these drive units according to the invention offers further advantages for medical use. All the drive units used for the motorized stand have this design in principle. A corresponding drive unit includes the drive motor proper (41), for example, a disk armature motor, and also gears (42). As already mentioned, an additional mechanical stabilization of the whole system is achieved by the suitable coordination of the gear frictions of all the drive units used. Suitable gears are, for example, sold by the firm HARMONIC DRIVE under the designation HDGM. In addition to the latitude for the instrument weight, this dimensioning of the gear frictions has the consequence that even a not exactly horizontal positioning does not influence the ability to operate. Moreover, each drive unit includes a brake (43) with which the position can be fixed at any time. A permanent magnet single disk brake can, e.g., be used for this purpose. Furthermore it is important from the aspect of safety that each drive unit include two angle transducers (44a, 44b). One of the two angle transducers (44a) is directly coupled to the drive motor (41), while the second angle transducer (44b) operates independently of the drive motor (41). In motorized operation, the use of two angle transducers ensures a mutual monitoring of the sensed angle data. Moreover the motorized stand can be able in principle to operate on possible failure of an angle transducer. Even on failure of the drive motor (41), coordinate sensing is in principle possible via the independent, second angle transducer. In addition, possible gear tolerances can thereby be compensated for. A commercial incremental angle transducer is used as the angle transducer (44a) coupled to the drive motor (41) in the illustrated embodiment, a prior reference measurement being always necessary for its use. A coded rotation transducer is used as a second, independent, angle transducer (44b), and supplies the continuous absolute angle measurement values of the respective joint motion. The use of a second angle transducer of this kind offers the advantage that after a possible failure of the first incremental angle transducer, no second referencing is required during the operation, but the present angle values are always directly available. Furthermore the position information at any time is ensured even when there is a failure of the drive unit. Suitable angle transducers for this purpose are, e.g., sold by the firm of HEIDENHAIN under the type designation ROC 417. A speed transducer (45) furthermore provides for the monitoring of the speed of travel of the respective element of the motorized stand.

All the elements of a drive unit are connected by corresponding signal leads to the control unit, which both reads in the present data and correspondingly evaluates the required control signals to be sent to the drive unit. A separate control circuit is provided for each drive unit, and controls the approach to given reference values.

I claim:

1. Motorized stand for positioning medical instruments, comprising a multi-joined mechanism having integrated angle transducers and individual drive units for individual joints of said multi-jointed mechanism, and a control unit, said multi-jointed mechanism being balanced at lest coarsely by mechanical balancing means, said mechanical balancing means comprising balancing weights and coordinated gear frictions of said drive units.

2. Motorized stand according to claim 1, wherein said mechanical balancing means comprises springs.

3. Motorized stand according to claim 1, wherein at least one control circuit is provided for each of said drive units, said control circuit being arranged for controlling approaching predetermined reference values.

4. Motorized stand according to claim 1, wherein said multi-joined mechanism comprises a plurality of axes about which driven rotation of said individual joints is arranged, a drive unit is provided for each said axis, and each of said drive units includes a drive motor with gears, a brake, a speed transducer, and two angle transducers.

5. Motorized stand according to claim 4, wherein said two angle transducers comprise an incremental angle transducer coupled to said drive motor of each drive unit and an angle transducer independent of said drive motor for supplying absolute angle values.

6. Motorized stand according to claim 1, wherein said control unit is arranged for continuously monitoring angle values of said angle transducers and determining from said angle values, coordinates of said medical instruments in the coordinate system of said motorized stand, said control unit having an input interface for defined provision of target coordinates.

7. Motorized stand according to claim 6, further comprising a foot portion on said motorized stand, said control unit being arranged above said foot portion.

8. Motorized stand according to claim 1 further comprising a foot portion with rollers, a motor drive for extending and retracting said rollers, and a vertical support column arranged on said foot portion.

9. Motorized stand according to claim 1 further comprising an operation microscope provided on said motorized stand as a medical instrument.

10. Motorized stand for positioning medical instruments, comprising a multi-jointed mechanism having integrated angle transducers and individual drive units for individual joints of said multi-jointed mechanism, and a control unit, said multi-jointed mechanism being balanced at least coarsely by mechanical balancing means, said multi-jointed mechanism comprising a plurality of axes about which driven rotation of said individual joints is arranged, further comprising a drive unit for each of said axes, each of said drive units including a drive motor with gears, a brake, a speed transducer and two angle transducers.

11. Motorized stand according to claim 10, wherein said mechanical balancing means is selected from the group consisting of springs and balancing weights.

12. Motorized stand according to claim 10, wherein at least one control circuit is provided for each of said drive units, said control circuit being arranged for controlling approaching predetermined reference values.

13. Motorized stand according to claim 10, wherein said two angle transducers comprise an incremental angle transducer coupled to said drive motor of each of said drive units and an angle transducer independent of said drive motor for supplying absolute angle values.

14. Motorized stand according to claim 10, wherein said drive units have gear frictions that are coordinated such that a mechanically balanced entire system results even when there is variation of weight of said medical instruments within a defined range.

15. Motorized stand according to claim 10, wherein said control unit is arranged for continuously monitoring angle values of said angle transducers and determining from said angle values, coordinates of said medical instruments in the coordinate system of said motorized stand, said control unit having an input interface for defined provision of target coordinates.

16. Motorized stand according to claim 15, further comprising a foot portion on said motorized stand, said control unit being arranged above said foot portion.

17. Motorized stand according to claim 10, further comprising a foot portion with rollers, a motor drive for extending and retracting said rollers, and a vertical support column arranged on said foot portion.

18. Motorized stand according to claim 10, further comprising an operation microscope provided on said motorized stand as a medical instrument.

19. Motorized stand for positioning medical instruments, comprising a multi-jointed mechanism having integrated angle transducers and individual drive units for individual joints of said multi-jointed mechanism, and a control unit, said multi-jointed mechanism being balanced at least coarsely by mechanical balancing means, wherein each of said drive units comprises an incremental angle transducer coupled to a drive motor of each drive unit and an angle transducer independent of said drive motor for supplying absolute angle values.

20. Motorized stand according to claim 19, wherein said mechanical balancing means is selected from the group consisting of springs and balancing weights.

21. Motorized stand according to claim 19, wherein at least one control circuit is provided for each of said drive units, said control circuit being arranged for controlling approaching predetermined reference values.

22. Motorized stand according to claim 19, wherein said multi-jointed mechanism comprises a plurality of axes about which driven rotation of said individual joints is arranged. and a drive units is provided for each of said axes, and includes a drive motor with gears, a brake, and a speed transducer.

23. Motorized stand according to claim 22, wherein said drive units have gear frictions that are coordinated such that a mechanically balanced entire system results even when there is variation of weight of said medical instruments within a defined range.

24. Motorized stand according to claim 19, wherein said control unit is arranged for continuously monitoring angle values of said angle transducers and determining from said angle values, coordinates of said medical instruments in the coordinate system of said motorized stand, said control unit having an input interface for defined provision of target coordinates.

25. Motorized stand according to claim 24, further comprising a foot portion on said motorized stand, said control unit being arranged above said foot portion.

26. Motorized stand according to claim 19, further comprising a foot portion with rollers, a motor drive for extending and retracting said rollers, and a vertical support column arranged on said foot portion.

27. Motorized stand according to claim 19, further comprising an operation microscope provided on said motorized stand as a medical instrument.

28. Motorized stand for positioning medical instruments, comprising a multi-jointed mechanism having integrated angle transducers and individual drive units for individual joints of said multi-jointed mechanism, and a control unit,
   said multi-jointed mechanism being balanced at least coarsely by mechanical balancing means,
   wherein each of said drive units includes a motor drive,
   further comprising a stand member arranged on a vertical support column and movable by one of said motor drives about a vertical axis, a parallelogram linkage together with at least one balancing weight arranged on said stand member or displacement by at least one of said motor drives about at least one horizontal axis, a first support arm with a longitudinal axis, arranged on said parallelogram linkage and movable by one of said motor drives about a second axis, a second support arm with a free end, arranged on said first support arm as an extension of said first support arm and movable by one of said motor drives about a third axis perpendicular to said longitudinal axis of said first support arm, a third support arm with a longitudinal axis and a free end, arranged at said free end of said second support arm and movable by one of said motor drives about its longitudinal axis, and an interface for a medical instrument arranged at said free end of said third support arm,
   wherein a drive unit is provided for each axis about which driven rotation is arranged, and each of said drive units includes a drive motor with gears, a brake, a speed transducer, and two angle transducers.

29. Motorized stand according to claim 28, wherein said two angle transducers comprise an incremental angle transducer coupled to said drive motor of each drive unit and an angle transducer independent of said drive motor for supplying absolute angle values.

30. Motorized stand according to claim 29, wherein said drive units have gear frictions that are coordinated such that a mechanically balanced entire system results even when there is variation of weight of said medical instruments within a defined range.

31. Motorized stand according to claim 28, wherein said control unit is arranged for continuously monitoring angle values of said angle transducers and determining from said angle values, coordinates of said medical instruments in the coordinate system of said motorized stand, said control unit having an input interface for defined provision of target coordinates.

32. Motorized stand according to claim 28, further comprising a foot portion on said motorized stand, said control unit being arranged above said foot portion.

33. Motorized stand according to claim 28, further comprising a foot portion with rollers, and a motor drive for extending and retracting said rollers.

34. Motorized stand according to claim 28, wherein said parallelogram linkage is displaceable by said motor drive both relative to at least one of said vertical support column and said stand member on which it is arranged, and to itself per se about at least one horizontal axis.

35. Motorized stand according to claim 28, wherein said parallelogram linkage includes at least one balancing weight having a weight such that said motorized stand is balanced in relation to motion about said horizontal axes of said parallelogram linkage.

36. Motorized stand according to claim 28, further comprising a second free end on said second support arm and at least one balancing weight arranged at aid second free end of said second support arm, wherein said first support arm is constructionally formed such that said motorized stand is balanced in respect of motion about at least one of said longitudinal axis of said first support arm and said axis perpendicular to said longitudinal axis of said first support arm about which second support arm is rotatable.

37. Motorized stand according to claim 28, wherein said first support arm is embodied in a double cranked construction.

38. Motorized stand according to claim 28, further comprising an operation microscope provided on said motorized stand as a medical instrument.

39. Motorized stand for positioning medical instruments, comprising a multi-jointed mechanism having integrated angle transducers and drive units for individual joints of said multi-jointed mechanism, and a control unit,
   said multi-jointed mechanism being balanced at least coarsely by mechanical balancing means,
   wherein each of said drive units includes a motor drive,
   further comprising a stand member arranged on a vertical support column and movable by one of said motor drives about a vertical axis, a parallelogram linkage together with at least one balancing weight arranged on said stand member for displacement by at least one of said motor drives about at least one horizontal axis, a first support arm with a longitudinal axis, arranged on said parallelogram linkage and movable by one of said motor drives about a second axis, a second support arm with a free end, arranged on said first support arm as an extension of said first support arm and movable by one of said motor drives about a third axis perpendicular to said longitudinal axis of said first support arm, a third support arm with a longitudinal axis and a free end, arranged at said free end of said second support arm and movable by one of said motor drives about its longitudinal axis, and an interface for a medical instrument arranged at said free end of said third support arm,
   wherein a drive unit is provided for each axis about which driven rotation is arranged, and each of said drive units includes a drive motor with gears, a brake, a speed transducer, and two angle transducers,
   further comprising a foot portion with rollers and a motor drive for extending and retracting said rollers, wherein said vertical support column is arranged on said foot portion.

* * * * *